US008901155B2

(12) United States Patent
Oki et al.

(10) Patent No.: US 8,901,155 B2
(45) Date of Patent: Dec. 2, 2014

(54) METHOD FOR TREATING A TRPV1-MEDIATED DISEASE

(71) Applicant: Santen Pharmaceutical Co., Ltd., Osaka (JP)

(72) Inventors: Kenji Oki, Ikoma (JP); Fumio Tsuji, Ikoma (JP); Chikako Setoguchi, Ikoma (JP); Iwao Seki, Ikoma (JP); Masaaki Murai, Ikoma (JP); Minoru Sasano, Ikoma (JP)

(73) Assignee: Santen Pharmaceutical Co., Ltd., Osaka-shi, Osaka (JP)

( * ) Notice: Subject to any disclaimer, the term of this patent is extended or adjusted under 35 U.S.C. 154(b) by 40 days.

(21) Appl. No.: 13/680,465

(22) Filed: Nov. 19, 2012

(65) Prior Publication Data

US 2013/0090359 A1    Apr. 11, 2013

Related U.S. Application Data

(62) Division of application No. 12/682,090, filed as application No. PCT/JP2008/068696 on Oct. 16, 2008, now abandoned.

(30) Foreign Application Priority Data

Oct. 16, 2007  (JP) ................................ 2007-268785

(51) Int. Cl.
*A61K 31/44*     (2006.01)
*C07D 213/36*    (2006.01)
*A61K 31/4409*   (2006.01)

(52) U.S. Cl.
CPC .......... *A61K 31/4409* (2013.01); *C07D 213/36* (2013.01); *A61K 31/44* (2013.01)
USPC ............................ 514/357; 546/285; 546/332

(58) Field of Classification Search
None
See application file for complete search history.

(56) References Cited

U.S. PATENT DOCUMENTS

| 7,098,226 | B2 | 8/2006 | Ban et al. |
| 7,345,064 | B2 | 3/2008 | Ban et al. |
| 7,491,739 | B2 | 2/2009 | Ban et al. |
| 2003/0032623 | A1 | 2/2003 | Ban et al. |

FOREIGN PATENT DOCUMENTS

| JP | 2002-53555 A | 2/2002 |
| JP | 2003-226686 A | 8/2003 |
| WO | WO 03/092670 A1 | 11/2003 |
| WO | WO 03/097586 A1 | 11/2003 |
| WO | WO 2005/040100 A1 | 5/2005 |
| WO | WO 2007/042906 A1 | 4/2007 |

OTHER PUBLICATIONS

International Search Report for PCT/JP 2008/068696, Jan. 6, 2009.
Supplemental European Search Report dated Oct. 25, 2010 for EP 08839876.
Zimmermann, M. et al., "Pathobiology of neuropathic pain," *European Journal of Pharmacology*, 429 (2001) 13-37.
Zhang et al., "The immune system: a new look at pain," *Chin. Med. J.*, 2006, 119(11), 930-938.
L.R. Watkins et al., Beyond Neurons: Evidence that immune and glial cells contribute to pathological pain states, *Physiol. Rev.*, 82: 981-1011, 2002.
Sommer, C. et al., "Anti-TNF-neutralizing antibodies reduce pain-related behavior in two different mouse models of paintul mononeuropathy," *Brain Research*, 913, (2001), 86-89.
Shinobu Tamura et al., "Tsukaku Dentatsu ni Okeru Enshosei Cytokine no Yakuwari," *Igaku no Ayumi*, 2004, vol. 211, No. 5, pp. 393-397.
Tadahito Shimada et al., "Shokakan Nenmaku Shogai to Cytokine," *Japanese Journal of Clinical Medicine*, 1998, vol. 56, No. 9, 27(2235) to 31(2239).
Noriyuki Masuda et al., "Hainyo Shogai Chiryoyaku no Kiso," *Folia Pharmacologica Japonica*, May 14, 2007. vol. 129, No. 5, pp. 361-367.
Kuo, H-C. et al., "Therapeutic effect of multiple resiniferatoxin intravesical instillations in patients with refractory detrusor overactivity: a randomized double-blind, placebo controlled study," *J. Urol.*, 2006, vol. 176, No. 2, pp. 641-645.
Yi Dai et al., "Capsaicin Juyotai no Yakuwari," *Igaku no Ayumi*, 2004, vol. 211, No. 5, pp. 389-392.
Masaaki Murai et al., "SA13353 (1-[2-(1-Adamantyl)ethyl]-1-pentyl-3-[3-(4-pyridyl)propyl]urea) inhibits TNF-α production through the activation of capsaicin-sensitive afferent neurons mediated via transient receptor potential vanilloid 1 in vivo," *European Journal of Pharmacology*, 2008, vol. 588, Issues 2-3, pp. 309-315.
T. Tsunoda and K. Hanaoka, "Physiological Mechanism of Pain Generation," *Igaku no Ayumi (Journal of Clinical and Experimental Medicine)*, vol. 195, No. 9, 2000.

(Continued)

*Primary Examiner* — Zinna Northington Davis
(74) *Attorney, Agent, or Firm* — Holtz, Holtz, Goodman & Chick PC (57) ABSTRACT

A method for treating a TRPV1-mediated disease by administering to a patient a therapeutically effective amount of a compound or a salt thereof having the following formula [I]:

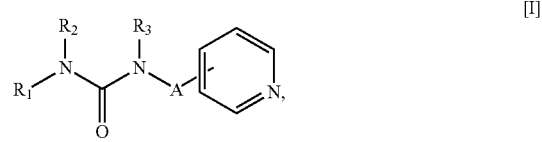

wherein A represents a lower alkylene group or a lower alkenylene group; $R_1$ represents a hydrogen atom, an unsubstituted or substituted alkyl group or an unsubstituted or substituted alkenyl group; and $R_2$ and $R_3$ are the same or different and represent a hydrogen atom, an unsubstituted lower alkyl group or a lower alkyl group substituted by a monocyclic cycloalkyl group, a polycyclic cycloalkyl group or an aryl group.

11 Claims, 6 Drawing Sheets

(56) References Cited

OTHER PUBLICATIONS

"Guidelines for Clinical Evaluation Methods of Drugs for Overactive Bladder," (Notification No. 0628001 of the Pharmaceutical Affairs and Food Sanitation Council of the Ministry of Health, Labour and Welfare), Jun. 28, 2006.

S. Kato et al., G.I. Research, "Role of sensory nerves and trpv1 in protection of upper gastrointestinal tract mucosa," vol. 13, No. 5, p. 367-374, (2005).

Extended European Search Report mailed Oct. 30, 2013, which issued in the counterpart European Patent Application No. 13003791.4-1464.

METHOD FOR TREATING A TRPV1-MEDIATED DISEASE

CROSS-REFERENCE TO RELATED APPLICATIONS

This application is a Divisional application of application Ser. No. 12/682,090 filed Apr. 8, 2010 (now abandoned), which is the United States national phase application of International application PCT/JP2008/068696 filed Oct. 16, 2008. The entire contents of each of application Ser. No. 12/682,090 and International application PCT/JP2008/068696 are incorporated by reference herein.

TECHNICAL FIELD

The present invention relates to a therapeutic agent for a TRPV1-mediated disease containing a urea derivative as an active ingredient.

BACKGROUND ART

TRPV1 is a nonselective cation channel which belongs to the transient receptor potential (TRP) superfamily, contains six transmembrane domains, and has high permeability of calcium ions, and is also called vanilloid receptor 1 (VR1) or capsaicin receptor. As agonists for TRPV1, vanilloids such as capsaicin which is a pungent component in hot chili peppers and resiniferatoxin which is a capsaicin derivative are known. On the other hand, as antagonists for TRPV1, compounds such as iodoresiniferatoxin and capsazepine are known.

TRPV1 is mainly located in sensory neurons, however, it is also expressed in non-neuronal tissues as well as neuronal tissues of epithelium, bone, bladder, gastrointestinal tract, lung, and many other visceral organs.

It is known that TRPV1 is activated by a noxious stimulus such as an acid (pH 5.9 or lower) or heat (43° C. or higher), and physiological effects brought about by activation of TRPV1 are diverse (see Non-patent document 1).

Pain is classified according to the mechanism of onset thereof into nociceptive pain (somatic pain and visceral pain), neuropathic pain (pain caused by nerve damage and occurring without a noxious stimulus), and the like.

Nociceptive pain is pain caused by tissue damage created by a stimulus such as a heat stimulus. Somatic pain is pain caused by activation of nociceptors in cutaneous or deep tissues, and is classified into superficial pain (skin or mucosa origin) and deep pain (muscle, bone, or joint origin). Somatic pain is characterized in that it is localized pain.

As compared with somatic pain, distribution and characteristics of visceral pain are often not clearly identified. It is considered that pain is transmitted through the course of afferent fibers along the autonomic nerves which control the internal organs.

Neuropathic pain is pathological pain caused by dysfunction of the peripheral or central nervous system itself. Neuropathic pain includes intermittent or paroxysmal severe pain as well as tonic pain with burning sensation or the like, and is characterized by accompanied by symptoms such as hypoesthesia, hyperalgesia and allodynia (see Non-patent document 2).

Overactive bladder is a pathological condition with a syndrome including urinary urgency, frequent urination, and urge incontinence. According to the epidemiological survey conducted by The Japan Neurogenic Bladder Society, the prevalence of overactive bladder in Japanese aged 40 years old or older is 12.4% and the total number of patients with overactive bladder is estimated to be about 8.1 million. The prevalence has a high correlation with aging, and the prevalence in those aged 70 years old or older reaches 30% or more. Further, it is shown that the quality of life (QOL) of patients with overactive bladder is remarkably decreased in a wide range including daily life and mental status.

As the cause of overactive bladder, neurogenic causes such as cerebrovascular disorder and spinal cord injury and non-neurogenic causes such as lower urinary tract obstruction are known. However, most cases are idiopathic and the cause of overactive bladder cannot be identified, and it is inferred that several factors are involved in the onset of overactive bladder in combination. The treatment of overactive bladder is mainly drug therapy, and particularly, a muscarinic receptor antagonist is used in the treatment as a first-line drug. However, a satisfactory therapeutic effect cannot be obtained in some patients, and medication compliance sometimes decreases due to discomfort such as dry mouth. Therefore, further development of a therapeutic agent for overactive bladder has been demanded (see Non-patent document 3 and Non-patent document 4).

The gastrointestinal mucosa is a large interface of an individual with the outside world and induces rapid and precise physiological responses to various stimuli and changes in the lumen to maintain the homeostasis thereof. The gastrointestinal tract such as stomach or duodenum is an organ which responds very sensitively to stress. In particular, stomach is exposed not only to mental stress and physical stress such as burn, injury, or surgery but also to many factors to cause mucosal damage including extrinsic factors such as food, alcohol, and drug and intrinsic factors such as gastric acid and bile, and therefore, the stomach is in an environment where mucosal damage is liable to occur.

As a typical intrinsic factor which takes a role in gastric mucosal defense mechanism, prostaglandin is known.

In the treatment of gastrointestinal dysfunction such as gastric ulcer, a compound which suppresses gastric acid secretion such as an $H_2$ receptor inhibitor is used, however, a problem that ulcer relapse occurs when administration is discontinued and the like may sometimes arise (see Non-patent document 5).

Further, it is considered that activation of the sympathetic nervous system by capsaicin via TRPV1 activates energy metabolism, which leads to fat burning, i.e., anti-obesity.

In light of such circumstances, studies have been conducted as to whether compounds having various activities can be applied to a therapeutic agent for a TRPV1-mediated disease, however, the results are not always satisfactory, and further searches for a therapeutic agent for a TRPV1-mediated disease have been demanded.

On the other hand, Patent document 1 describes that a urea derivative which is an active ingredient in the present invention has an inhibitory action on the production of TNF-α and can be used as a therapeutic agent for an autoimmune disease such as rheumatoid arthritis (RA)

Patent document 1: JP-A-2002-53555

Non-patent document 1: Dai, T. and Noguchi, K., Igaku no Ayumi (Journal of Clinical and Experimental Medicine), 2004, Vol. 211, No. 5, pp. 389-392

Non-patent document 2: Igaku no Ayumi (Journal of Clinical and Experimental Medicine), Vol. 195, No. 9, 2000, 582-584, physiological Mechanism of pain generation, Tsunoda, T. and Hanaoka, K.

Non-patent document 3: Guideline for Clinical Evaluation Methods of Drugs for Overactive Bladder (Notification No. 0628001 of the Pharmaceutical Affairs and Food Sanitation Council of the Ministry of Health, Labour and Welfare)

Non-patent document 4: Folia Pharmacologica Japonica, Vol. 229, No. 5, pp. 361-367

Non-patent document 5: Kato, S. et al., G. I. Research, Vol. 13, p. 367, 2005

DISCLOSURE OF THE INVENTION

Problems to be Solved

It is an interesting object to search for a compound suitable as a therapeutic agent for a TRPV1-mediated disease, particularly pain, overactive bladder, or gastrointestinal dysfunction, and to find a novel pharmaceutical use of a known urea derivative.

Means for Solving the Problems

Therefore, the present inventors focused on known urea derivatives represented by the following general formula [I] useful as a medicine (JP-A-2002-53555) and conducted studies to search for a therapeutic agent for a TRPV1-mediated disease.

As a result, these urea derivatives are found to be a TRPV1 agonist. Further, these urea derivatives are found to be useful as a therapeutic agent for TRPV1-mediated disease, particularly pain, overactive bladder, or gastrointestinal dysfunction because the derivatives have a therapeutic effect in experimental models of pain, overactive bladder, and gastrointestinal dysfunction, thereby accomplishing the present invention.

The invention relates to a therapeutic agent for a TRPV1-mediated disease, containing a compound represented by the following general formula [I] or a salt thereof (hereinafter, referred to as "the present compound" unless otherwise stated) as an active ingredient.

[I]

[wherein, A represents a lower alkylene group or a lower alkenylene group; $R_1$ represents a hydrogen atom, an alkyl group which may have a substituent or an alkenyl group which may have a substituent; and $R_2$ and $R_3$ are the same or different and represent a hydrogen atom or a lower alkyl group which may be substituted by a monocyclic cycloalkyl group, a polycyclic cycloalkyl group, or an aryl group.]

The present compound represented by the above general formula [I] has an inhibitory effect on renal ischemic injury and is useful as a therapeutic agent for a TRPV1-mediated disease such as acute renal failure or chronic renal failure.

BEST MODE FOR CARRYING OUT THE INVENTION

Hereinafter, the respective groups defined in the general formula [I] will be described in detail.

The lower alkylene group refers to an alkylene group having 1 to 6 carbon atoms such as a methylene group, a methylmethylene group, an ethylene group, a methylethylene group, a trimethylene group, a tetramethylene group, a methyltetramethylene group, a pentamethylene group, or a hexamethylene group. The alkylene group may be substituted by a lower alkyl group, i.e., may be a branched alkylene group; preferably, the lower alkylene group refers to a straight alkylene group having 1 to 6 carbon atoms, and the alkylene group may be substituted by one or more methyl groups; more preferably, the lower alkylene group refers to a straight alkylene group having 1 to 6 carbon atoms and may be substituted by one methyl group.

The lower alkenylene group refers to an alkenylene group having one or more double bonds and having 2 to 6 carbon atoms such as a vinylene group, a propenylene group, a butenylene group, or a pentenylene group. The alkenylene group may be substituted by a lower alkyl group, i.e., may be a branched alkenylene group; preferably, the lower alkenylene group refers to a straight alkenylene group having 2 to 6 carbon atoms, and the alkenylene group may be substituted by one or more methyl groups; more preferably, the lower alkenylene group refers to a straight alkenylene group having 2 to 6 carbon atoms and may be substituted by one methyl group.

The alkyl group refers to a straight or branched alkyl group having 1 to 12 carbon atoms such as a methyl group, an ethyl group, a propyl group, a butyl group, a hexyl group, an octyl group, a decyl group, a dodecyl group, an isopropyl group, an isobutyl group, an isopentyl group, an isohexyl group, an isooctyl group, a t-butyl group, or a 3,3-dimethylbutyl group.

The lower alkyl group refers particularly to a straight or branched alkyl group having 1 to 6 carbon atoms among the alkyl groups, and preferably refers to a straight alkyl group having 1 to 6 carbon atoms.

The alkenyl group refers to a straight or branched alkenyl group having 2 to 12 carbon atoms such as a vinyl group, an allyl group, a 3-butenyl group, a 5-hexenyl group, or an isopropenyl group, and is preferably a straight or branched alkenyl group having 2 to 6 carbon atoms, and is particularly preferably a straight alkenyl group having 2 to 6 carbon atoms.

The monocyclic cycloalkyl group refers to a cycloalkyl group having 3 to 10 carbon atoms such as a cyclopropyl group, a cyclobutyl group, a cyclopentyl group, a cyclohexyl group, a cycloheptyl group, a cyclooctyl group, or a cyclodecyl group, preferably refers to a cycloalkyl group having 5 to 7 carbon atoms, and more preferably refers to a cyclohexyl group.

The polycyclic cycloalkyl group refers to a polycyclic cycloalkyl group having 4 to 10 carbon atoms such as an adamantyl group, preferably refers to a polycyclic cycloalkyl group having 10 carbon atoms, and more preferably refers to an adamantyl group.

The aryl group refers to an aromatic hydrocarbon ring such as a phenyl group or a naphthyl group, and preferably refers to a phenyl group.

The halogen atom refers to a fluorine atom, a chlorine atom, a bromine atom, or an iodine atom, and preferably refers to a fluorine atom.

The substituent refers to, for example, a halogen atom, a trihalogenomethyl group, a lower alkyl group, a cycloalkyl group, an aryl group, a heterocyclic group, or a methoxy group, preferably refers to a halogen atom, a trihalogenomethyl group, a cyclohexyl group, a phenyl group, a furanyl group, a thiophenyl group, a thiazolyl group, or a morpholino group, and more preferably refers to a trihalogenomethyl group.

The salt according to the invention is not particularly limited insofar as the salt is pharmaceutically acceptable, and examples thereof include salts with an inorganic acid such as hydrochloric acid, nitric acid, sulfuric acid, or phosphoric acid, salts with an organic acid such as acetic acid, fumaric acid, maleic acid, succinic acid, or a tartaric acid, and salts with an alkaline metal or an alkaline earth metal such as sodium, potassium, or calcium. Further, quaternary ammonium salts of the present compound are also included in the salt according to the invention. Further, in the case where a geometrical isomer or an optical isomer are/is present in the present compound, such isomers are also encompassed in the scope of the present invention. In addition, the present compound may be in the form of a hydrate or a solvate.

In the compounds represented by the above general formula [I], a preferred compound to be used in the therapeutic agent for a TRPV1-mediated disease of the invention is a compound, in which 1) A is a lower alkylene group or a lower alkenylene group;
2) $R_1$ is a lower alkyl group which may have a substituent; and
3) $R_2$ is a hydrogen atom, and $R_3$ is a lower alkyl group substituted by a monocyclic cycloalkyl group, a polycyclic cycloalkyl group, or an aryl group; or
$R_3$ is a hydrogen atom, and $R_2$ is a lower alkyl group substituted by a monocyclic cycloalkyl group, a polycyclic cycloalkyl group, or an aryl group.

In the compounds represented by the above general formula [I], a more preferred compound to be used in the therapeutic agent for a TRPV1-mediated disease of the invention is a compound, in which 1) A is a lower alkylene group;
2) $R_1$ is a lower alkyl group which may have a substituent;
3) $R_3$ is a hydrogen atom; and
4) $R_2$ is a lower alkyl group substituted by a monocyclic cycloalkyl group or a polycyclic cycloalkyl group.

Here, the lower alkyl group substituted by a monocyclic cycloalkyl group or a polycyclic cycloalkyl group is preferably a straight lower alkyl group substituted by a monocyclic cycloalkyl group or a polycyclic cycloalkyl group.

In the compounds represented by the above general formula [I], a further more preferred compound to be used in the therapeutic agent for a TRPV1-mediated disease of the invention is a compound, in which A is a trimethylene group or a methyltrimethylene group; $R_1$ is a straight lower alkyl group which may have a substituent; $R_2$ is an adamantylethyl group or an adamantylpropyl group; and $R_3$ is a hydrogen atom.

The therapeutic agent for a TRPV1-mediated disease according to the invention contains, as an active ingredient, a compound selected from the group consisting of:
1-[2-(1-adamantyl)ethyl]-1-pentyl-3-[3-(4-pyridyl)propyl] urea (Compound 1),
1-[2-(1-adamantyl)ethyl]-3-[3-(4-pyridyl)propyl]-1-(3,3,3-trifluoropropyl)urea (Compound 2),
1-[3-(1-adamantyl)propyl]-1-propyl-3-[3-(4-pyridyl) propyl]urea (Compound 3),
1-[2-(1-adamantyl)ethyl]-3-[1-methyl-3-(4-pyridyl)propyl]-1-pentylurea (Compound 4),
1-[2-(1-adamantyl)ethyl]-3-[2-methyl-3-(4-pyridyl)propyl]-1-pentylurea (Compound 5),
(+)-1-[2-(1-adamantyl)ethyl]-3-[2-methyl-3-(4-pyridyl)propyl]-1-pentylurea (Compound 6), and
(E)-1-[2-(1-adamantyl)ethyl]-1-pentyl-3-[3-(4-pyridyl)-2-propenyl]urea (Compound 7) as preferred specific compounds among the compounds represented by the above general formula [I], or a salt thereof.

A therapeutic agent for a TRPV1-mediated disease containing, as an active ingredient, 1-[2-(1-adamantyl)ethyl]-1-pentyl-3-[3-(4-pyridyl)propyl]urea among the above-mentioned Compounds 1 to 7, or a salt thereof is particularly preferred.

The structural formulae of the typical compounds included in the present compound are shown below.

TABLE 1

TABLE 1-continued

Compound 6

Compound 7

The present compound can be prepared by, for example, the method described in JP-A-2002-53555.

The term "pain" as used in the specification and claims refers to any pain regardless of its nature.

The term "vanilloid receptor" as used in the specification refers to any vanilloid receptor such as TRPV1 or TRPV2.

In order to study the usefulness of the present compound, first, it was confirmed whether or not the present compound is a TRPV1 agonist. As will be described in detail in the section of "Pharmacological Test" below, the present compound exhibited higher binding affinity for a neuronal membrane specimen containing TRPV1 than capsaicin which is a known agonist. Further, the action of the present compound of promoting release of a neurotransmitter from a neuronal terminal was antagonized by capsazepine which is a TRPV1 antagonist. The assay results showed that the present compound is an excellent TRPV1 agonist.

Examples of the disease mediated by TRPV1, i.e., the TRPV1-mediated disease include pain, overactive bladder, gastrointestinal dysfunction, obesity, hiccup, thermal burn caused by exposure to heat, chemical burn caused by exposure to an acid, and sunburn. Since the present compound has an excellent TRPV1 agonistic action, the compound is useful for the treatment of these TRPV1-mediated diseases and is particularly useful as a therapeutic agent for pain, overactive bladder, or gastrointestinal dysfunction among these diseases.

It was confirmed that the present compound is useful as a therapeutic agent for a disease mediated by TRPV1 by pharmacological tests.

Pain is sensory information essential to the living body for perceiving a noxious stimulus from the external world and recognizing the site of a lesion. TRPV1 is mainly located in nerve terminals and is an ion channel receptor activated by a noxious stimulus such as an acid (pH 5.9 or lower) or heat (43° C. or higher). By the activation of TRPV1, a neuropeptide such as substance P or CGRP is released from a nerve terminal, which is considered to be involved in transmission of pain signals.

It is known that depletion of these neuropeptides in nerve terminals is one of the methods of blocking transmission of pain signals. For example, it is known that a TRPV1 agonist such as capsaicin induces depletion of these neuropeptides in nerve terminals. In fact, capsaicin is clinically used in the treatment of pain, particularly nociceptive pain such as pain which accompanies inflammation and lasts for a long time. Further, it has been reported that capsaicin can be used also in the treatment of neuropathic pain in the study using a model of sciatic nerve injury (Rashid H. et al., The Journal of Pharmacology and Experimental Therapeutics Vol. 304, p. 940, 2003).

Examples of the kind of pain to be treated by a TRPV1 agonist include nociceptive pain, neuropathic pain, visceral pain, somatic pain, acute pain, chronic pain, pain accompanying burn caused by an acid or heat, toothache, general headache, migraine, cluster headache, and neuralgia.

As will be described in detail in the section of "Pharmacological Test" below, when the analgesic effect of the present compound was studied using an acetic acid writhing model, the present compound suppressed the number of writhes and was found to have an excellent analgesic effect. That is, the present compound which is a TRPV1 agonist is useful as a therapeutic agent for pain, for example, nociceptive pain, neuropathic pain, visceral pain, somatic pain, acute pain, chronic pain, pain accompanying burn caused by an acid or heat, toothache, general headache, migraine, cluster headache, and neuralgia, and particularly useful as a therapeutic agent for nociceptive pain, neuropathic pain, visceral pain, or somatic Pain.

Recently, an expression of TRPV1 was confirmed in urothelial cells, and the relationship between micturition and TRPV1 is being elucidated. Further, it has been reported that a TRPV1 agonist is also effective in both neurogenic and non-neurogenic overactive bladder, and Kuo et al. has reported that a TRPV1 agonist such as resiniferatoxin is clinically useful for the treatment of overactive bladder (Kuo, H. et al., The Journal of Urology Vol. 176, pp. 641-645, 2006).

The activity of the present compound as a therapeutic agent for overactive bladder was studied using a rat model with continuous intravesical infusion of saline. As will be described in detail in the section of "Pharmacological Test" below, the present compound exhibited a remarkable TRPV1 agonistic activity and exhibited an excellent effect of prolonging the micturition interval in the rat model with continuous intravesical infusion of saline, and therefore is useful as a therapeutic agent for overactive bladder, particularly urinary urgency, frequent urination, or urge incontinence. The present compound is useful as a therapeutic agent particularly for neurogenic or non-neurogenic overactive bladder. Examples of the neurogenic overactive bladder include overactive bladder accompanying disorder of the central nervous system found above the pons in the brainstem (such as cerebrovascular disorder, Parkinson's disease, multiple system atrophy, dementia, brain tumor, encephalitis, or meningitis) or spinal cord disorder (such as spinal cord injury, multiple sclerosis, spinocerebellar ataxia, spinal cord tumor, cervical spondylosis, ossification of posterior longitudinal ligament, spinal stenosis, spinal vascular disorder, myelitis, or spina bifida), and examples of the non-neurogenic overactive bladder include overactive bladder accompanying lower urinary tract obstruction, overactive bladder accompanying aging, overactive bladder accompanying pelvic floor weakening, and idiopathic overactive bladder.

Further, it is known that a TRPV1 agonist such as capsaicin releases a transmitter such as CGRP from the terminals of sensory neurons which control the gastrointestinal tract. CGRP released by the activation of TRPV1 increases the blood flow rate in the gastrointestinal mucosa by the action of improving microcirculation, and further, it has also been noted that CGRP exhibits an action of protecting the gastrointestinal mucosa by, for example, promoting mucus secretion via a transmitter such as NO or $PGI_2$ and acts in an inhibitory manner on gastrointestinal dysfunction via such a transmitter (Harada N. et al., Progress in Medicine Vol. 22, p. 1997, 2002), (Kato S. et al., G.I. Research Vol. 13, p. 367, 2005).

The activity of the present compound as a therapeutic agent for gastrointestinal dysfunction was studied using rat models for gastrointestinal mucosal blood flow rate and gastrointestinal dyfunction. As will be described in detail below, the present compound is a TRPV1 agonist and exhibited an excellent action of increasing the mucosal blood flow and an excellent therapeutic effect on gastric mucosal injury. Therefore, the present compound is useful as a therapeutic agent for gastrointestinal dysfunction, particularly upper gastrointestinal dysfunction such as gastric ulcer, duodenal ulcer, anastomotic ulcer, reflux esophagitis, non-erosive gastroesophageal reflux disease, upper gastrointestinal hemorrhage, acute gastritis, or chronic gastritis.

The present compound can be administered parenterally or orally. Examples of the dosage form include a tablet, a capsule, a granule, a powder, an injection, a plaster, an ointment, a lotion, a suspension, and an intravesical infusion. Preparation examples of the present compound are described in JP-A-2002-53555 and JP-A-2003-226686, however, a preparation method is not limited to the methods described in these patent documents and the present compound can be formulated into a preparation using a widely used technique. For example, an oral preparation such as a tablet, a capsule, a granule, or a powder can be prepared by optionally adding a dilluting agent such as lactose, microcrystalline cellulose, starch, or a vegetable oil; a lubricant such as magnesium stearate or talc; a binder such as hydroxypropyl cellulose or polyvinylpyrrolidone; a disintegrant such as carboxymethylcellulose calcium or low-substituted hydroxypropylmethylcellulose; a coating agent such as hydroxypropylmethylcellulose, macrogol, or a silicone resin; or a film forming agent such as a gelatin film to the present compound.

The dose of the present compound can be properly changed depending on symptoms, age, dosage form, and the like. In the case of an oral preparation, it can be administered once or divided into several times generally at a dose of from 0.1 to 5000 mg, preferably from 1 to 1000 mg per day.

EXAMPLES

Preparation Example

General preparation examples of the present compound as an oral preparation and an injection are shown below.
1) Tablet
Formulation 1 (in 100 mg)

| Present compound | 1 mg |
| Lactose | 66.4 mg |
| Corn starch | 20 mg |
| Carxboxymethylcellulose calcium | 6 mg |
| Hydroxypropylcellulose | 4 mg |
| Magnesium stearate | 0.6 mg |

A tablet of the above-mentioned formulation is coated using 2 mg of a coating agent (for example, a conventional coating agent such as hydroxypropylmethylcellulose, macrogol, or a silicone resin), whereby an objective coated tablet can be obtained (the same shall apply to a tablet of a formulation below). In addition, a desired tablet can be obtained by appropriately changing the amounts of the present compound and the additives.
2) Capsule
Formulation 1 (in 150 mg)

| Present compound | 5 mg |
| Lactose | 145 mg |

A desired capsule can be obtained by appropriately changing the mixing ratio of the present compound to lactose.
3) Injection
Formulation 1 (in 10 ml)

| Present compound | 10 to 100 mg |
| Sodium chloride | 90 mg |
| Sodium hydroxide | q.s. |
| Hydrochloric acid | q.s. |
| Sterile purified water | q.s. |

A desired injection can be obtained by appropriately changing the mixing ratio of the present compound to the additives.

Hereinafter, the results of pharmacological tests using the present compound will be shown, however, these examples are for understanding the invention well and are not meant to limit the scope of the invention.
Pharmacological Test
1. Binding Activity of the Present Compound in Rat Spinal Cord Membrane Specimen It is known that TRPV1 is expressed in sensory neurons in rat spinal cord. Szallasi et al. have reported the binding of resiniferatoxin which is a TRPV1 agonist to a vanilloid receptor contained in a membrane specimen, and also have reported the results of a competition assay with capsazepine which is a capsaicin antagonist, using a rat spinal cord neuronal membrane specimen (Journal of Pharmacology and Experimental Therapeutics, Vol. 267, pp. 728-733). According to the method of Szallasi et al., the binding activity of the present compound to a vanilloid receptor contained in a rat spinal cord membrane specimen was studied.
(Preparation of Test Compound-Containing Liquid, etc.)

A test compound-containing liquid and a competitive compound-containing liquid containing a test compound and a competitive compound, respectively, and each composed of purified water containing 1% DMSO were prepared. As the competitive compound, tritium-labeled resiniferatoxin ($^3$H-RTX) was used, and the concentration of $^3$H-RTX in the competitive compound-containing liquid was set to 0.2 nM.
(Preparation of Membrane Specimen)

Rat spinal cord was homogenized according to a common procedure, and the resulting homogenate was washed several times, followed by centrifugation. The resulting pellet was suspended in an incubation buffer (10 mM HEPES, pH 7.4, 0.25 mg/ml ESA, 0.75 mM $CaCl_2$, 5 mM KCl, 2 mM $MgCl_2$, 5.8 mM NaCl, 137 mM sucrose) at 10 mg/mL, whereby a membrane specimen was prepared.
(Binding Assay)

After 5.25 µL of the test compound-containing liquid and 500 µL of the membrane specimen were mixed, 20 µL of the competitive compound-containing liquid was added thereto, and the entire resulting mixture was incubated at 37° C. for 60 minutes. The resulting membrane/$^3$H-RTX complex was collected by filtration, followed by washing. Then, the radioactivity was measured with a scintillation counter.

(Analysis of Assay Results)

The above-mentioned assay was performed using the test compound-containing liquids containing a test compound at various concentrations and the results were analyzed as follows.

The inhibition ratio (%) of the test compound at each concentration was obtained from the following equation.

(Inhibition ratio(%))={1−[(binding activity in the presence of test compound (cpm))−(radioactivity of non-specific binding (cpm))]/[(radioactivity of total binding (cpm))−(radioactivity of non-specific binding (cpm))]}×100

Subsequently, the inhibition ratios at the respective concentrations were plotted and a 50% inhibitory concentration ($IC_{50}$) and a Hill coefficient were obtained by a nonlinear regression analysis. As the regression equation, the following two-parameter logistic equation was used.

$Y$=bottom+(top−bottom)/{1+10^[(Log $IC_{50}$−$X$)×Hill coefficient]}

In the equation, X represents the logarithm of concentration of the compound; and Y represents the inhibition ratio (%). Y changed from bottom to top following a sigmoid curve. The inhibition ratios of 0% and 100% were defined bottom and top, respectively.

Further, the inhibition constant (Ki value) was obtained from the following equation.

$Ki$=$IC_{50}$/(1+(radiolabeled-ligand concentration)/(dissociation constant)

In the equation, for the dissociation constant, a dissociation constant established in the same assay system (0.046 nM as the vanilloid receptor) was used.

As the thus obtained assay results of the present compound, the assay results of Compound 1 are shown as an example.

Figure 1:
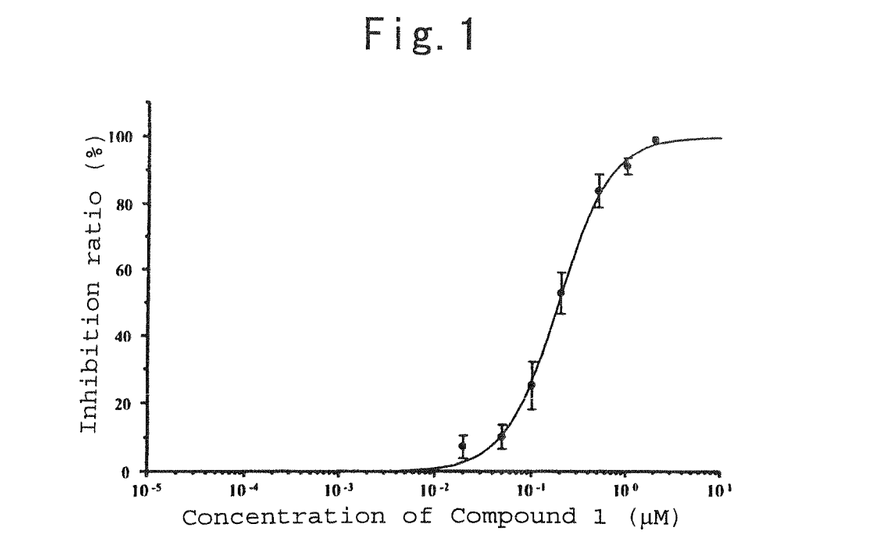
FIG. 1 is a graph showing the inhibition curve of Compound

The inhibition curve of Compound 1 is as shown in FIG. 1, and the $IC_{50}$ value, Ki value, and Hill coefficient of Compound 1 to the vanilloid receptor in the rat spinal cord neuronal membrane specimen were 191±28 nM (mean±SEM of assays performed in triplicate), 35.8±5.2 nM, and 1.83±0.449, respectively. Further, the $IC_{50}$ value and Ki value of capsaicin obtained in the same assay system were 3.14±0.76 µM and 0.587±0.142 µM, respectively. From these results, it was shown that the present compound has extremely high binding affinity for the vanilloid receptor as compared with capsaicin which is a known agonist.

2. Effect of Present Compound on TRPV1 Agonist-Induced CGRP Release System Using Rat Dorsal Root Ganglion-Derived Neurons It is known that TRPV1 is expressed in dorsal root ganglion (DRG), and that by the activation of TRPV1, CGRP which is a neurotransmitter is released from a nerve terminal. According to the method of Ahluwalia et al., (European Journal of Neuroscience, Vol. 17, p. 2611, 2003), the CGRP releasing activity of the present compound in cultured neurons derived from rat DRG was studied.

(Preparation of Test Compound-Containing Liquid, etc.)

A test compound was weighed and dissolved in DMSO. The resulting solution was diluted with a medium, whereby a test compound-containing liquid was prepared. Each test compound-containing liquid was prepared such that 0.4% DMSO was contained therein as well. As a positive control, capsaicin which is a TRPV1 agonist was used, and as a competitive compound against the test compound, capsazepine which is a TRPV1 antagonist was used, and a competitive compound-containing liquid was prepared in the same manner.

(Assay Method)

A dorsal root ganglion isolated from the spinal cord of a rat was sectioned and enzymatically treated with a collagenase/DNase I solution at 37° C. for 1 hour, and then with a trypsin/DNase I solution at 37° C. for 20 minutes. The released neurons were washed and collected, and then seeded in a poly-D-lysine/laminin-coated culture dish and cultured under conditions of 37° C. and 5% $CO_2$ in a neuronal medium (NGF/NCS medium) supplemented with a nerve growth factor for 1 day. The medium was replaced with an NGF/NCS medium containing cytosine arabinoside, and the neurons were further cultured for 2 days. The medium was replaced with an NGF/NCS medium, and the neurons were cultured for 1 day. Then, the neurons were cultured for 30 minutes in the presence or absence of capsazepine, and thereafter, Compound 1 was added to the medium and the neurons were cultured for 10 minutes. Then, the culture supernatant was collected.

The measurement of CGRP in the culture supernatant was performed using a commercially available ELISA-based assay kit according to the protocol attached to the kit. In the assay, each group consisted of 3 rats, and a mean and SEM of the CORP concentration in the culture supernatant in each group were obtained. Statistical analysis was performed with Student's t-test or Dunnett's multiple comparison.

(Assay Results)

Figure 2:
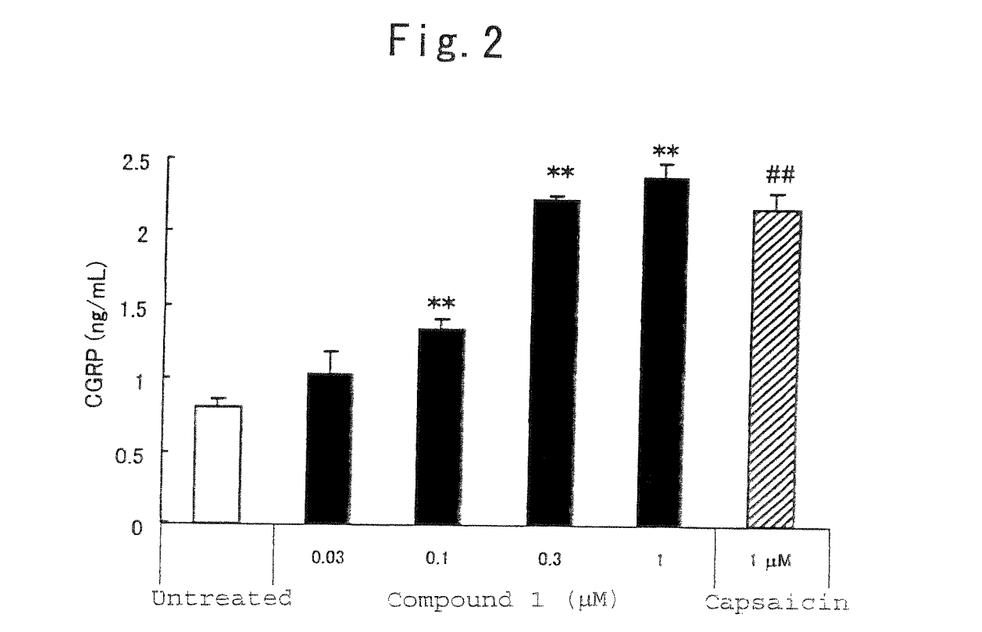
FIG. 2 is a graph showing the results (mean±SEM) of studying the dose responsiveness on CGRP release of Compound 1 in the absence of capsazepine.
Figure 3:
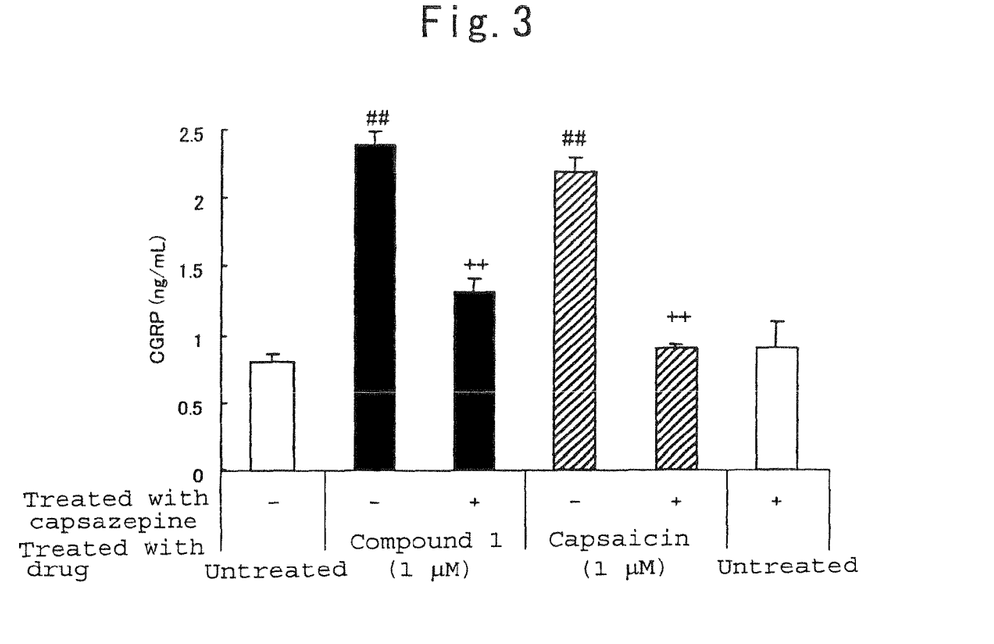
FIG. 3 is a graph showing the results of a competitive inhibition assay for the CGRP releasing action of Compound 1 using 10 μM (final concentration) capsazepine.

As examples of the assay results, the results (mean±SEM) of studying dose responsiveness on CGRP release of Compound 1 in the absence of capsazepine are shown in FIG. 2, and the results (mean±SEM) of a competitive inhibition assay for the CGRP releasing action of Compound 1 using 10 µM (final concentration) capsazepine are shown in FIG. 3. In these figures, ## indicates that the P value for comparison with the untreated group by Student's t-test is 1% or less; ** indicates that the P value for comparison with the untreated group by Dunnett's multiple comparison is 1% or less; and ++ indicates that the P value for comparison with the compound-treated group by Student's t-test is 1% or less.

As is apparent from FIG. 2, Compound 1 released CGRP in a dose-dependent manner and exhibited a CGRP releasing action with a potency comparable to that of capsaicin which is the positive control at a lower concentration than that of capsaicin. On the other hand, as is apparent from FIG. 3, the CGRP release by Compound 1 was antagonized by capsazepine to an extent comparable to that observed in the case of capsaicin. From the assay results, it was shown that the present compound is an agonist specific to TRPV1.

From the results of the pharmacological tests described above, it is shown that the present compound is an excellent TRPV1 agonist.

3. Measurement of Intracellular Calcium Influx by Present Compound in Human TRPV1-Expressing Cells It is known that TRPV1 is an ion channel receptor and by the activation of TRPV1, intracellular calcium ion influx occurs. According to the method of Phelps et al. (Eur. J. Pharmacol., 513: 57-66, 2005), the action of the present compound of activating human TRPV1 was studied using CHO cells transfected with a gene encoding human TRPV1.

(Preparation of Test Compound-Containing Liquid, etc.)

CHO cells were suspended in DMEM and seeded in a culture plate at $3.5 \times 10^4$ cells/well. A test compound or a control compound was dissolved in DMSO to prepare a DMSO solution, and times concentrated test compound-containing liquid and control compound-containing liquid each of which was composed of HBSS and contained the thus prepared DMSO solution were prepared. As the control compound, capsaicin was used, and the control compounds and the test compounds in the control compound-containing liquid and in the test compound-containing liquid were set to 10 μM, respectively.

(Calcium Influx Assay)

To the CHO cells, a calcium indicator was added, and the resulting mixture was incubated at 37° C. for 30 minutes, and then further incubated at 22° C. for 30 minutes to achieve equilibration. Subsequently, one-tenth volume of the test compound-containing liquid, control compound-containing liquid (final concentration: 1 μM), or HBSS solution was added thereto, and a change in the fluorescence intensity of the intracellular calcium concentration indicator was measured.

(Analysis of Assay Results)

The ratio of the fluorescence intensity when stimulation with the test compound was applied to that when stimulation with 1 μM capsaicin used as the control compound was applied is obtained from the following equation, which is expressed as a percentage.

(Calcium influx(%))=((fluorescence intensity in the presence of test compound)−(background fluorescence intensity)/(fluorescence intensity in the presence of control compound)−(background fluorescence intensity))×100

The thus obtained assay results of the present compound are shown in Table 2.

TABLE 2

| Compound | Calcium influx (%) |
| --- | --- |
| Compound 2 | 74.1 |
| Compound 3 | 59.8 |
| Compound 4 | 43.9 |
| Compound 5 | 64.3 |
| Compound 6 | 76.6 |
| Compound 7 | 36.1 |

4. Assay for Analgesic Effect of Present Compound by Acetic Acid Writhing Method As a method of evaluating the analgesic effect of a drug, a mouse acetic acid writhing method by Anderson et al. is widely used (Fed. Proc., Vol. 18, p. 412, 1959). Accordingly, a test for antinociceptive action of a test compound was performed using the mouse acetic acid writhing method, and the analgesic effect of the test compound was evaluated and studied.

(Preparation of 0.7% Acetic Acid Solution)

Saline was added to 99.7% acetic acid, whereby a 0.7% acetic acid solution was prepared.

(Assay Method)

20 minutes after oral administration of the test compound, the 0.7% acetic acid solution was intraperitoneally administered in a proportion of 0.1 ml per 10 g of mouse body weight. Then, the number of writhes occurring between 10 minutes and 20 minutes after the administration of acetic acid was counted to measure the antinociceptive action of the test compound.

(Assay Results)

Figure 4:
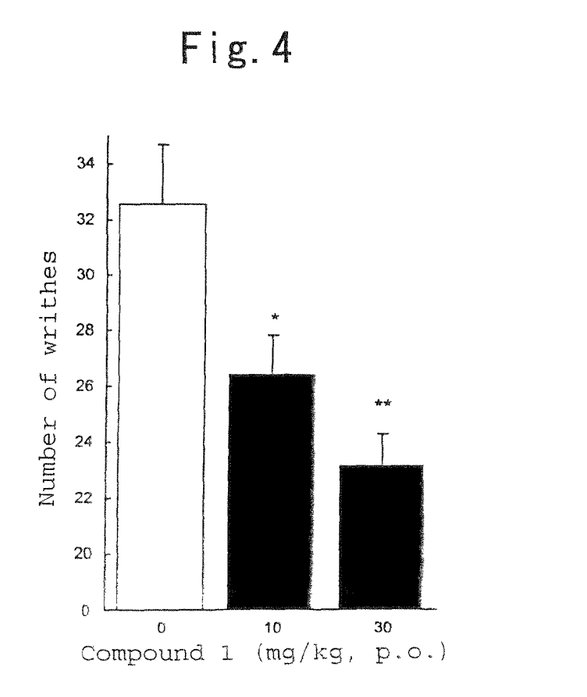
FIG. 4 is a graph showing the antinociceptive action of Compound 1 (mean+SEM).

As an example of the assay results, the antinociceptive action of Compound 1 (mean+SEM) is shown in FIG. 4. In FIG. 4, * indicates that the P value for comparison with the untreated group (Compound 0 mg/kg treated group) by Dunnett's multiple comparison is less than 5%; and ** indicates that the P value for comparison with the untreated group by Dunnett's multiple comparison is less than 1%.

As is apparent from FIG. 4, the present compound suppressed the number of writhes in a dose-dependent manner in the acetic acid writhing model.

From the results of the pharmacological test described above, it is shown that the present compound exhibits an excellent therapeutic effect on pain, particularly an inhibitory effect on nociceptive pain and is useful as a therapeutic agent for pain.

5. Action of Present Compound of Prolonging Micturition Interval in Rat Model With Continuous Intravesical Infusion of Saline As a method of evaluating a therapeutic effect on overactive bladder, measurement of action of prolonging the micturition interval in a model with continuous intravesical infusion of saline by Yu et al. is widely used (journal of Pharmacology and Experimental Therapeutics, 290, 825 (1999)). According to the method of Yu et al., measurement of the action of a test compound of prolonging the micturition interval in a model with continuous intravesical infusion of saline was performed, and the therapeutic effect of the test compound on overactive bladder was evaluated and studied.

(Preparation of Test Compound-Containing Liquid)

A test compound was dissolved in saline containing 1% polyoxyethylene castor oil (Cremophor EL), whereby a test compound-containing liquid was prepared.

(Preparation of Comparative Control Agent)

Oxybutynin hydrochloride which is a control agent was dissolved in saline, whereby a control agent-containing liquid was prepared.

(Used Animal)

CD rats (male, 8 week old) were quarantined and acclimated for 1 week and divided into groups consisting of 2 to 6 rats and used in the assay.

(Assay Method)

Each rat was anesthetized with urethane (1.2 g/kg). A first catheter for infusion of an agent was inserted into the femoral vein of the rat and ligated thereto. An incision of about 2 cm was made along the midline of the abdomen and the bladder was exteriorized. Then, a puncture was made with a 19-G needle at the top of the bladder, and a second catheter for continuous infusion of saline was inserted into the bladder through the puncture and ligated thereto. The second catheter was connected to a three-way stopcock, and a 25-mL syringe (which was mounted on a syringe pump) for intravesical infusion of saline was connected to one opening of the three-way stopcock, and a pressure transducer was connected to the other opening.

(Measurement of Micturition Interval)

As for the measurement of micturition interval, a micturition pressure was continuously recorded, and the time point when the micturition pressure rapidly decreased in a micturition pressure chart was defined as the time point of micturition, and the interval between the time points was defined as the micturition interval and used in the analysis.

Saline was continuously infused into the bladder by the syringe pump at a rate within a range of from 2.4 to 4.8 mL/hr such that a stable micturition reflex was attained. A vehicle was infused into a femoral vein through the first catheter and the micturition interval was measured. At an appropriate time later, it was confirmed that the micturition interval became constant, and the test compound or the comparative control agent was infused in the same manner and the micturition interval was measured.

(Evaluation of Results)

As for the respective cases of administering the vehicle and the drug, a mean value of the micturition interval which was measured twice was calculated for each animal and defined as the micturition interval for the animal, and a mean value of the micturition interval was calculated for each group. A statistical analysis was performed using a paired t-test.

Figure 5:
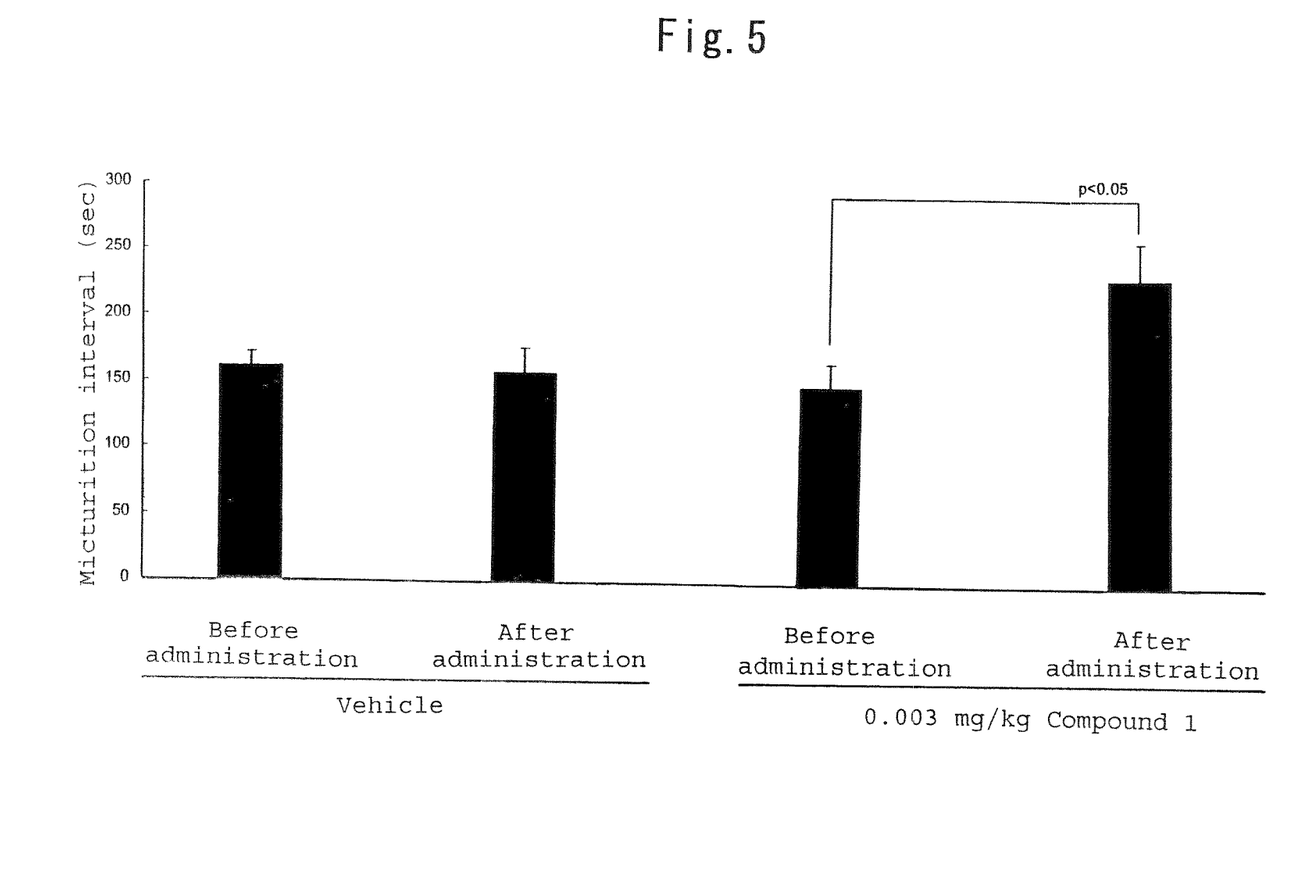
FIG. 5 is a graph showing the micturition interval in the case of Compound 1.
Figure 6:
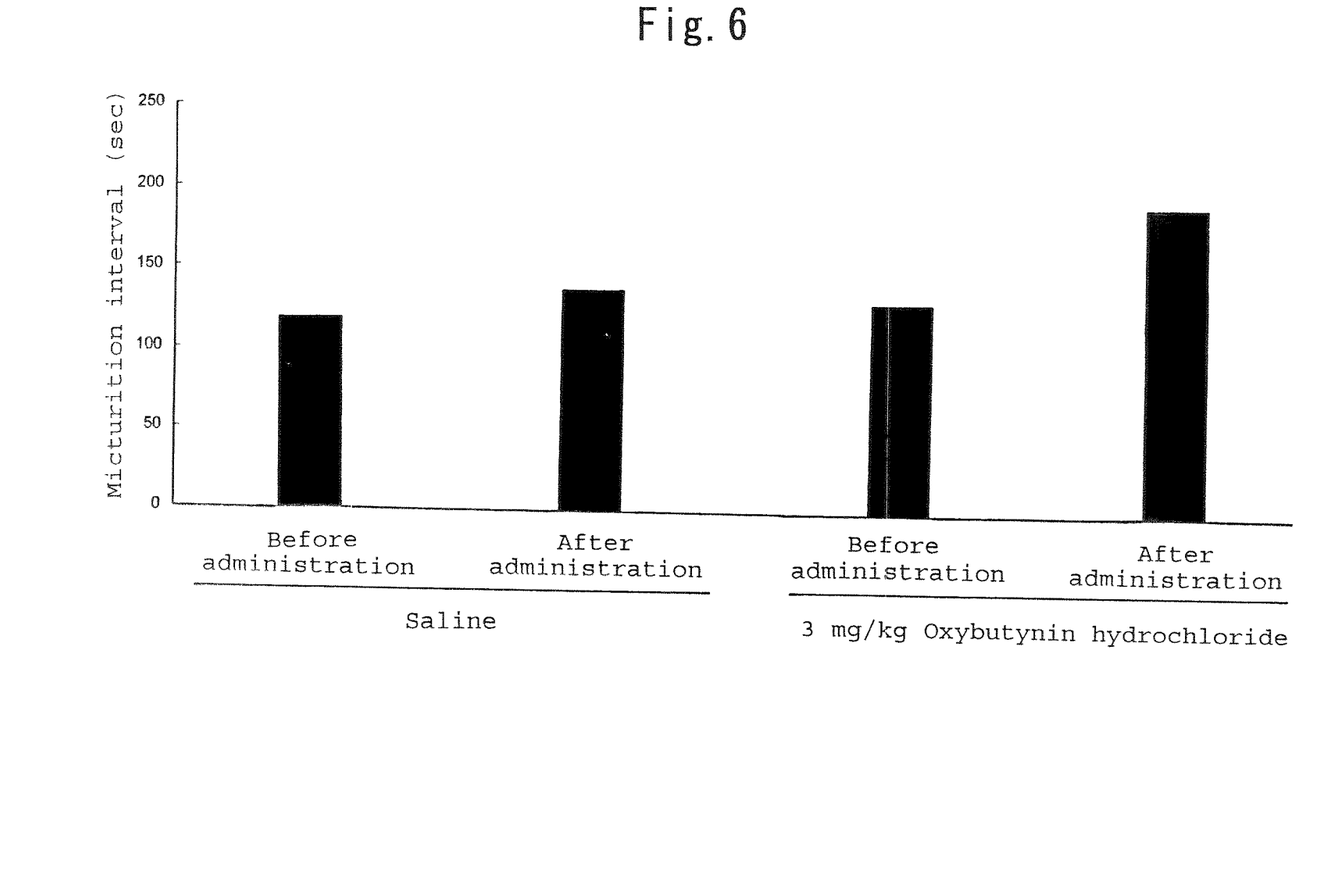
FIG. 6 is a graph showing the micturition interval in the case of the comparative control agent.

As examples of the test results, the micturition interval in the case of Compound 1 is shown in FIG. 5, and the micturition interval in the case of the comparative control agent is shown in FIG. 6.

As is apparent from FIGS. 5 and 6, the present compound exhibited an excellent action of prolonging the micturition interval at an extremely low dose and the potency was higher than that of oxybutynin hydrochloride which is clinically used as a therapeutic agent for overactive bladder.

From the results of the pharmacological test described above, it is shown that the present compound exhibits an extremely excellent action of prolonging the micturition interval and is useful as a therapeutic agent for overactive bladder.

6. Action of Present Compound of Increasing Blood Flow Rate for Gastrointestinal Mucosal Blood Flow in Normal Rat An action of increasing the gastrointestinal mucosal blood flow rate in a normal animal is a model used in the evaluation of drug efficacy of a therapeutic agent for peptic ulcer, etc. Matsumoto et al. studied the action of capsaicin of increasing gastric mucosal blood flow using the above-mentioned method (Japanese Journal of Pharmacology, Vol. 57, p. 205, 1991). According to the method of Matsumoto, the action of the present compound of increasing the gastric mucosal blood flow rate in a normal rat was evaluated.

(Preparation of Test Compound-Containing Liquid)

A test compound-containing liquid was prepared immediately before use by suspending a test compound in a 1% aqueous methyl cellulose solution which is a vehicle.

(Assay Method)

In the measurement of mucosal blood flow rate, a laser tissue blood flow meter (OMEGAFLO FLO-N1) was used, and the blood flow rate was obtained as a blood flow rate per tissue weight.

A rat fasted for 18 hours or more was subjected to laparotomy under urethane anesthesia and the stomach was exteriorized and mounted on a perfusion chamber. Then, an incision was made along the greater curvature such that bleeding was not caused and gastric contents were washed away. Then, the stomach was stretched on the perfusion chamber and a probe of the laser blood flow meter was placed near the center of the lesser curvature. The stomach was perfused with saline until the gastric mucosal blood flow rate became stable, and the blood flow rate when the blood flow rate was maintained at a constant value was defined as a blood flow rate before treatment. The perfusion was stopped once and saline was removed completely. Then, the test compound-containing liquid was instilled thereinto and the blood flow rate was measured for 60 minutes.

(Evaluation of Results)

The blood flow rate before treatment and the gastric mucosal blood flow rate every 5 minutes after the treatment with the test compound were recorded for each animal.

Figure 7:
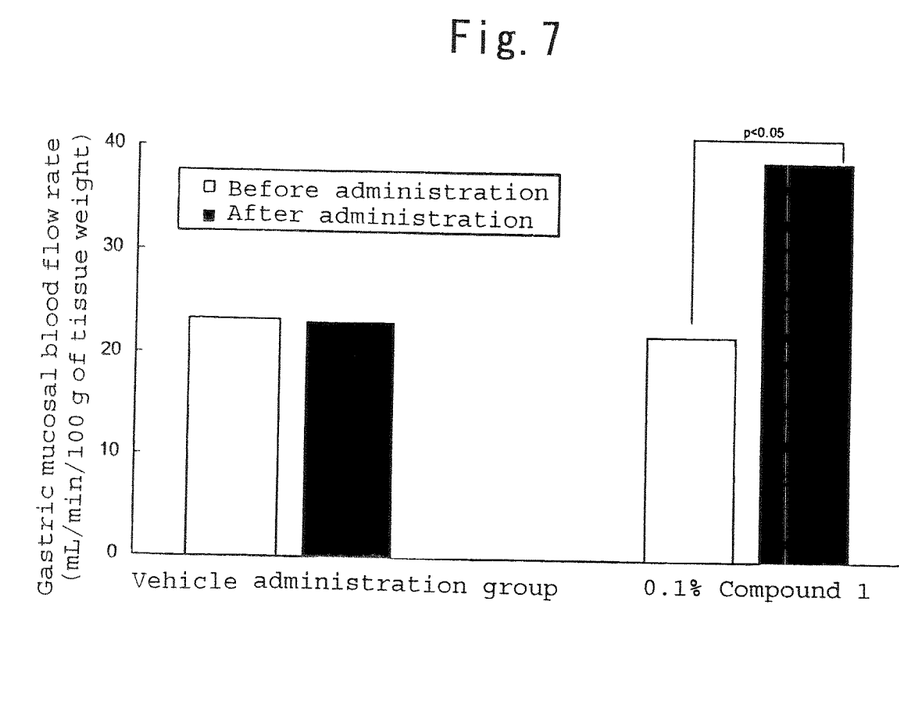
FIG. 7 is a graph showing the mean values of the maximum values of the measurements of the blood flow rates before and after treatment in the case of performing the treatment with only a vehicle (1% methyl cellulose) and the blood flow rates before and after treatment in the case of performing the treatment with the Compound 1-containing liquid.

As an example of the action of the present compound of increasing the gastrointestinal mucosal blood flow, the action of Compound 1 of increasing the gastric mucosal blood flow rate is shown. FIG. 7 shows the mean values of the respective maximum values of the measurements of the blood flow rates before and after treatment in the case of performing the treatment with only a vehicle (1% methyl cellulose) and the blood flow rates before and after treatment in the case of performing the treatment with the Compound 1-containing liquid. A statistical analysis was performed using a paired t-test.

As is apparent from FIG. 7 the present compound exhibited a marked action of increasing gastric mucosal blood flow.

7. Effect in Rat Model of Gastrointestinal Dysfunction

A model of indomethacin-induced gastric mucosal injury is a model of gastrointestinal dysfunction widely used in the evaluation of drug efficacy of a therapeutic agent for ulcer. According to the method of Hoshino et al. (Folia Pharmacologica Japonica, Vol. 97, p. 287, 1991), the effect of the present compound in a rat model of indomethacin-induced gastric mucosal injury was studied.

(Preparation of Test Compound-Containing Liquid, etc.)

A test compound-containing liquid was prepared immediately before use by suspending a test compound in a 1% aqueous methyl cellulose solution which is a vehicle. In the same manner, a control compound-containing liquid was prepared using, as a control compound, omeprazole which is a proton pump inhibitor and is clinically used as a therapeutic agent for peptic ulcer.

(Assay Method)

To a rat fasted for 24 hours, the test compound-containing liquid, control compound-containing liquid, or vehicle (pathological control group) was orally administered, and immediately thereafter, indomethacin (Wako Pure Chemical Industries, Ltd.) was subcutaneously administered at a dose of 30 mg/kg. A group in which the same procedure was performed except that the treatment with indomethacin was not performed was defined as a normal control group. 6 hours after the treatment with indomethacin, a 5 Chicago Sky Blue GB solution was intravenously injected through a tail vein and the rat was euthanized. Then, the stomach was excised and an incision, was made along the greater curvature. The stomach was washed with saline and semi-fixed with a 1% neutral formalin solution. The length of the longest diameter of the site of a lesion dyed in blue including an ecchymosis was measured macroscopically using calipers.

(Evaluation of Results)

A mean value of the sum of the longest diameters of the sites of lesions was obtained for each animal and was defined as an ulcer index. Further, a ratio of inhibition of gastric mucosal injury was calculated from the following equation.

(Ratio of inhibition of gastric mucosal injury(%))={−
[(ulcer index of compound administration
group)−(ulcer index of normal control group)]/
[(ulcer index of pathological control group)−
(ulcer index of normal control group)]}×100

Figure 8:
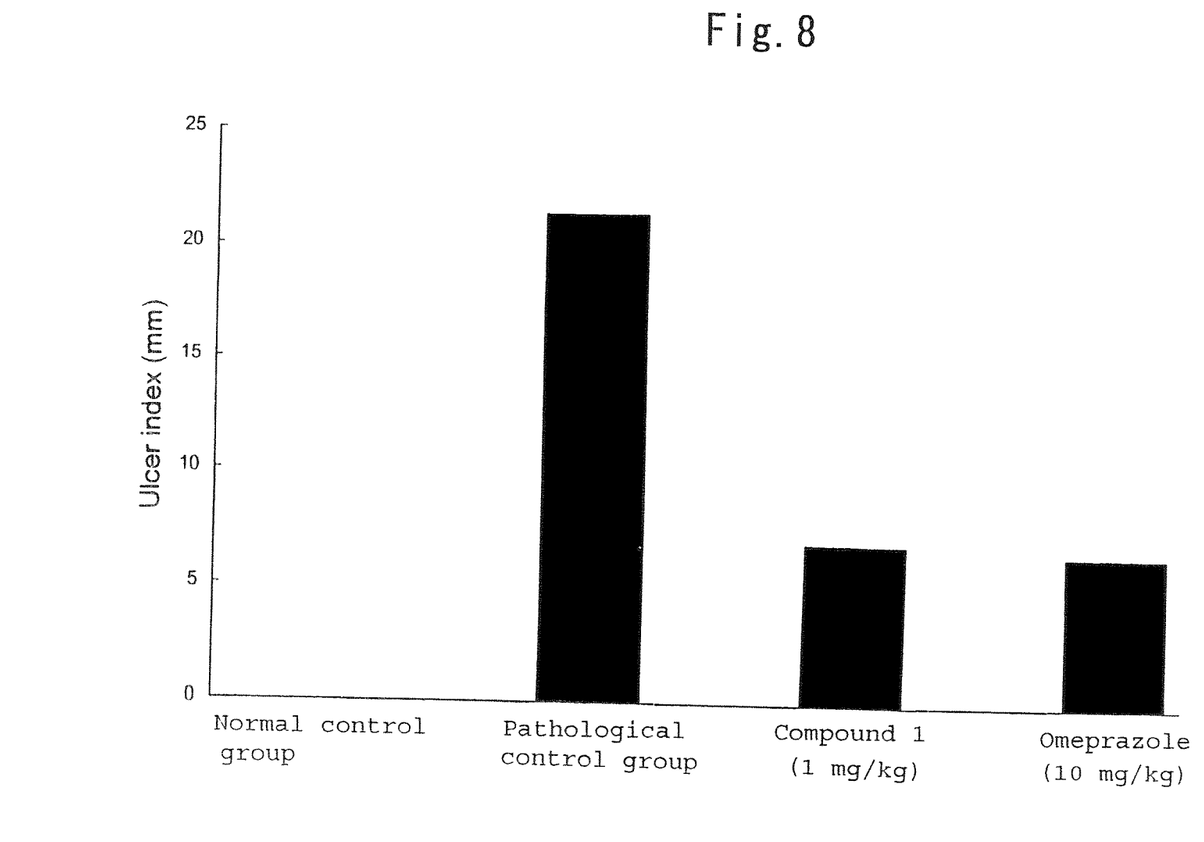
FIG. 8 is a graph showing an inhibitory effect of Compound 1 on indomethacin-induced gastric mucosal injury.

As an example of the inhibitory effect of the present compound on gastrointestinal dysfunction, the inhibitory effect of Compound 1 on indomethacin-induced gastric mucosal injury is shown in FIG. 8, and the ratio of inhibition of gastric mucosal injury obtained as described above is shown in Table 3.

TABLE 3

| Compound | inhibition ratio (%) |
| --- | --- |
| Compound 1 (1 mg/kg) | 67.41 |
| Omeprazole (10 mg/kg) | 69.22 |

As is apparent from FIG. 8 and Table 3, the present compound exhibited a remarkable effect that it exhibited an action of inhibiting gastric mucosal injury with a potency comparable to that of omeprazole which is a therapeutic agent for peptic ulcer at a lower dose than that of omeprazole.

From the results of the pharmacological test described above, it is shown that the present compound is extremely effective as a therapeutic agent for gastrointestinal dysfunction.

INDUSTRIAL APPLICABILITY

The present compound is a TRPV1 agonist and has a therapeutic effect in experimental models of pain, overactive bladder, and gastrointestinal dysfunction, and therefore is useful as a therapeutic agent for a TRPV1-mediated disease, particularly pain, overactive bladder, or gastrointestinal dysfunction.

The invention claimed is:

1. A method for treating a TRPV1-mediated disease, comprising administering to a patient a therapeutically effective amount of a compound, or a salt thereof, represented by the following formula [I]:

[I]

wherein A represents a lower alkylene group or a lower alkenylene group; $R_1$ represents a hydrogen atom, an unsubstituted or substituted alkyl group or an unsubstituted or substituted alkenyl group; and $R_2$ and $R_3$ are the same or different and represent a hydrogen atom, an unsubstituted lower alkyl group or a lower alkyl group substituted by a monocyclic cycloalkyl group, a polycyclic cycloalkyl group or an aryl group, wherein the TRPV1-mediated disease is selected from the group consisting of pain, an overactive bladder and a gastrointestinal dysfunction.

2. The method according to claim 1, wherein
A is a lower alkylene group or a lower alkenylene group;
$R_1$ is an unsubstituted or substituted lower alkyl group; and
$R_2$ is a hydrogen atom, and
$R_3$ is a lower alkyl group substituted by a monocyclic cycloalkyl group, a polycyclic cycloalkyl group or an aryl group; or
$R_3$ is a hydrogen atom, and $R_2$ is a lower alkyl group substituted by a monocyclic cycloalkyl group, a polycyclic cycloalkyl group or an aryl group.

3. The method according to claim 1, wherein
A represents a lower alkylene group;
$R_1$ represents an unsubstituted or substituted alkyl group;
$R_2$ represents an unsubstituted lower alkyl group or a lower alkyl group which is substituted by a monocyclic cycloalkyl group, a polycyclic cycloalkyl group or an aryl group; and
$R_3$ is a hydrogen atom.

4. The method according to claim 2, wherein
A is a lower alkylene group;
$R_1$ is an unsubstituted or substituted lower alkyl group;
$R_2$ is a lower alkyl group substituted by a monocyclic cycloalkyl group or a polycyclic cycloalkyl group; and
$R_3$ is a hydrogen atom.

5. The method according to claim 4, wherein A is a trimethylene group or a methyltrimethylene group; $R_1$ is a straight lower alkyl group which may have a substituent; $R_2$ is an adamantylethyl group or an adamantylpropyl group; and $R_3$ is a hydrogen atom.

6. The method according to claim 1, wherein A is a lower alkylene group, $R_1$ is an unsubstituted alkyl group or a substituted alkyl group, $R_2$ is an unsubstituted lower alkyl group or a lower alkyl group substituted with a substituent selected from the group consisting of a monocyclic cycloalkyl group, a polycyclic cycloalkyl group and an aryl group.

7. The method according to claim 1, wherein the compound is selected from the group consisting of:
1-[2-(1-adamantyl)ethyl]-1-pentyl-3-[3-(4-pyridyl)propyl]urea,
1-[2-(1-adamantyl)ethyl]-3-[3-(4-pyridyl)propyl]-1-(3,3,3-trifluoropropyl)urea,
1-[3-(1-adamantyl)propyl]-1-propyl-3-[3-(4-pyridyl)propyl]urea,
1-[2-(1-adamantyl)ethyl]-3-[1-methyl-3-(4-pyridyl)propyl]-1-pentylurea,
1-[2-(1-adamantyl)ethyl]-3-[2-methyl-3-(4-pyridyl)propyl]-1-pentylurea and
(+)-1-[2-(1-adamantyl)ethyl]-3-[2-methyl-3-(4-pyridyl)propyl]-1-pentylurea.

8. The method according to claim 1, wherein the compound is 1-[2-(1-adamantyl)ethyl]-1-pentyl-3-[3-(4-pyridyl)propyl]urea.

9. The method according to claim 1, wherein the TRPV1-mediated disease is pain.

10. The method according to claim 1, wherein the TRPV1-mediated disease is an overactive bladder.

11. The method according to claim 1, wherein the TRPV1-mediated disease is a gastrointestinal dysfunction.

* * * * *